United States Patent [19]

Marcus

[11] 4,187,286

[45] Feb. 5, 1980

[54] CONTRACEPTIVE SUPPOSITORY

[75] Inventor: Bertram J. Marcus, Freehold, N.J.

[73] Assignee: G&W Laboratories, Inc., South Plainfield, N.J.

[21] Appl. No.: 960,077

[22] Filed: Jan. 2, 1979

[51] Int. Cl.² .......................... A61K 9/02; A61K 9/46
[52] U.S. Cl. ........................................ 424/44; 424/78; 424/361; 128/271; 424/DIG. 14
[58] Field of Search .................... 424/14, 44, 78, 361, 424/363, DIG. 14; 128/271

[56]  References Cited

U.S. PATENT DOCUMENTS

| Re. 29,102 | 1/1977 | Schorm | 424/44 |
|---|---|---|---|
| 1,878,766 | 9/1932 | Fitzgerald | 424/44 |
| 2,191,139 | 2/1940 | Bibbins | 424/361 X |
| 2,584,166 | 2/1952 | Stevenson et al. | 424/14 |
| 2,623,839 | 12/1952 | Taub | 424/363 X |
| 2,623,840 | 12/1952 | Taub | 424/363 X |
| 2,623,841 | 12/1952 | Taub | 424/363 X |
| 2,854,377 | 9/1958 | Elias | 424/44 |
| 3,062,715 | 11/1962 | Reese | 424/44 |
| 3,121,663 | 2/1964 | Parker | 424/44 |
| 3,234,091 | 2/1966 | Lang et al. | 424/14 |

FOREIGN PATENT DOCUMENTS 28-147  1/1953  Japan.

OTHER PUBLICATIONS

Becker American Prof. Pharmacist 20(10):939–944,987, Oct. 1954, "Thickening Agents Used in Pharmacy".

*Primary Examiner*—Shep K. Rose
*Attorney, Agent, or Firm*—Arthur A. Jacobs

[57]  ABSTRACT

A suppository especially adapted for vaginal insertion to act as a contraceptive which comprises a mixture of polyethylene glycol, a spermicidally-active ingredient, a thickening agent, an effervescent agent and alginic acid, the action of the alginic acid reacting with the effervescent agent in moist conditions to form carbon dioxide and also forming a viscous barrier adherent to the vaginal walls to prevent penetration of the sperm.

10 Claims, No Drawings

CONTRACEPTIVE SUPPOSITORY

This invention relates to contraceptive agents, and it particularly relates to contraceptive suppositories adapted for vaginal insertion.

It has, heretofore, been proposed to use vaginal suppositories for contraceptive purposes. In this respect, U.S. Pat. No. 3,062,715 discloses vaginal tablets comprising effervescent powder and colloidal substances to effect a rapid decomposition and dissolution of the tablets; but the effectiveness of the composition depends on the presence of sufficient natural secretions which, when not present, results in incomplete dissolution and, therefore, insufficient protection. German Pat. No. 893,997 discloses a vaginal spermicidal agent comprising a wax-type barrier and a spermicide, whereby the carrier is adapted to melt after insertion and acts with the body liquids to form as emulsion in which the spermicide is dispersed. However, the dispersion is generally non-homogeneous and this non-homogeniety adversely effects the protection. Aerosol foams have also been used, but this not only requires specific apparatus, such as an insertion tube, but the amount inserted varies considerably with the user, and therefore, a sufficient amount may not be used for satisfactory results.

U.S. Pat. No. Re 29,102 discloses a vaginal tablet which somewhat overcomes many of the aforesaid disadvantages; however, this tablet, which generates a spermicide-containing foam when inserted in the vagina, is deficient in that it does not sufficiently stabilize the foam, so that if intercourse does not take place within a relatively short time after application, the protection is diminished. Furthermore, the generated foam does not effect a high degree of obstruction to sperm penetration beyond the foam barrier.

It is, therefore, one object of the present invention to provide a vaginal suppository contraceptive agent which is highly effective for extended periods of time after application and which does not depend on the amount of fluid present in the vagina.

Another object of the present invention is to provide a contraceptive suppository of the aforesaid type which forms an increased barrier against sperm penetration relative to other such suppositories.

Other objects of the present invention will be apparent from the following specification and claims.

In accordance with the present invention, a vaginal contraceptive suppository device is provided which contains one or more polyethylene glycols, a thickening agent such as microcrystalline cellulose, an effervescent agent such as sodium bicarbonate, a hydrophilic colloidal polysaccharide, such as alginic acid, which reacts with the sodium bicarbonate in aqueous condition to generate carbon dioxide, and a spermicide.

The spermicide is preferably nonoxynol-9, a nonylphenol polyglycol ether containing about 9 moles of ethylene oxide. One such product is produced by the Onyx Chemical Company, Jersey City, N.J., under the name "Neutronyx 600." It is present in the composition in a proportion of between about 3.6 and 4.4 percent by weight.

The alginic acid is, as stated above, a colloidal polysaccharide, more specifically, a polymer of beta-anhydro-d-mannuronic acid derived from seaweed. It is present in a proportion of about 13.5–16.5 percent by weight. This acid is an essential element of the present invention because it not only helps generate carbon dioxide when reacted with sodium bicarbonate, thereby causing effervescence, but it also imparts a clinging barrier of medium viscosity to the vaginal walls, and, in combination with the thickening agent, stabilizes the foam, thereby providing a most effective sperm barrier. The increased viscosity also makes sperm penetration more difficult. In addition, this polysaccharide imparts a controlling effect on the foam generation and is, furthermore, non-toxic,.

The sodium bicarbonate should be present in a proportion of about 10.8–13.2 percent by weight. Although not as preferable, potassium biphosphate may be substituted, but is not as preferable because it reacts more slowly.

The thickening agent should be present in a proportion of about 0.9–1.1 percent by weight. Although microcrystalline cellulose is preferable as the thickening agent, because it is very fine and is very hygroscopic, other substances may be methyl cellulose, carboxymethylcellulose, polyvinyl pyrrolidone or sodium alginate. A preferred material is "Avicel RC591", a combination of microcrystalline cellulose and the sodium salt of carboxymethyl cellulose, manufactured by FMC. This is preferable because the small amount of carboxymethyl cellulose gives additional swelling effect, although too much would be deleterious.

The polyethylene glycols may be varied as desired, but are preferably present in a proportion of about 61.2–74.8 percent by weight of the total composition.

The gas generating combination of the polysaccharide and the sodium bicarbonate should preferably constitute about 24.3–29.7 percent by weight of the composition.

The polyethylene glycols should contain a higher molecular weight material to provide a relatively high melting point and a harder suppository, and a lower molecular weight material to provide more facile disintegration. Preferably, the polyethylene glycols should include one of 1000 molecular weight and one of 300 molecular weight, but the 300 molecular weight material, which is used to permit more rapid and easier disintegration of the suppository, should be kept to a minimum, i.e. between about 3.2 and 4 percent by weight of the total polyethylene glycol ingredients. Over about 4 percent, the composition would become unduly tacky. If very hard suppositories are desired, some of the 1000 molecular weight material may be replaced by polyethylene glycol of 4000 molecular weight, but this is generally not desirable.

The folloiwng examples illustrate the invention:

EXAMPLE 1

| Components | Percent by weight |
| --- | --- |
| polyethylene glycol 1000 | 65.0 |
| polyethylene glycol 300 NF | 3.0 |
| "Avicel RC 591" | 1.0 |
| alginic acid (80 mesh) | 15.0 |
| sodium bicarbonate (100 mesh) | 12.0 |
| nonoxynol-9 | 4.0 |

The two polyethylene glycols are melted toether at a temperature of about 62°–68° C. When the melt is complete, the nonoxynol-9 is added to the melt under agitation, the agitation being continued for sufficient time to totally mix the ingredients, usually from about 5 to 10 minutes. The "Avicel RC 591" is then dispersed into the mixture under slow-speed agitation, after which first the sodium dicarbonate and then the alginic acid is added. Agitation is continued for about 15 to 30 minutes to completely disperse the latter ingredients into the mixture. During this period, the temperature is maintained substantially constant. Thereafter, the mass is cooled to about 52° C and is then poured into torpedo-shaped molds which have been pre-chilled to about 15°–20° C. The molds are then placed in freezing cabinets until the mass is thoroughly chilled. The products are thereafter removed from the molds, ready for use or storage.

EXAMPLE 2

| Components | Percent by Weight |
|---|---|
| polyethylene glycol 1000 | 53.0 |
| polyethylene glycol 300 | 11.7 |
| "Avicel RC-591" | 1.0 |
| "Methocel E4M" (methyl cellulose) | 1.0 |
| alginic acid | 16.7 |
| sodium bicarbonate | 13.3 |
| nonoxynol-9 | 3.3 |

The "Methocel E4M" is a methyl cellulose produced by the Dow Chemical Co., Midland, Mich., It is here substituted for an equal proportion of the high molecular weight polyethylene glycol.

The above ingredients are mixed together in the manner described in Example 1 and treated at the temperature and for the periods described in Example 1, the cellulose and methyl cellulose being utilized as one ingredient in place of the cellulose by itself.

Although the invention has been described above as constituting a vaginal delivery system for a spermicide such as nonoxynol-9, it may be used as a suppository delivery system for rectal rather than vaginal insertion. In such instances it may be used for a variety of active ingredients utilizable for various purposes. Among such active ingredients would be bisacodyl, used as a laxative, aminopylline, used as a smooth muscle relaxant (bronchialor), acetaminophen, used as an analgesic, and aspirin, used as an analgesic.

The invention claimed is:
1. A suppository consisting essentially of polyethylene glycol, a thickening agent, alginic acid, an effervescent agent and a medicinally active ingredient, the polyethylene glycol being present in a proportion of about 61.2–74.8 percent by weight, the thickening agent being present in a proportion of about 0.9–1.1 percent by weight, the effervescent agent being present in a proportion of about 10.8–13.2 percent by weight, the alginic acid being present in a proportion of about 13.5–16.5 percent by weight, and the medicinally active ingredients being present in a proportion of about 3.6–4.4 percent by weight.

2. The suppository of claim 1 wherein the polyethylene glycol is a mixture of at least two different molecular weight polyethylene glycols, one having a molecular weight of about 300 and at least one other having a molecular weight of about 1000.

3. The suppository of claim 1 wherein the thickening agent is a member of the group consisting of microcrystalline cellulose, methyl cellulose, carboxymethyl cellulose, polyvinyl pyrrolidone, sodium alginate, and mixtures thereof.

4. The suppository of claim 1 wherein the effervescent agent is a member of the group consisting of sodium bicarbonate and potassium biphosphate.

5. The suppository of claim 1 wherein the medicinally active agent is a spermicide.

6. The suppository of claim 5 wherein the spermicide is nonoxynol-9.

7. The suppository of claim 1 wherein the suppository is vaginally-insertable.

8. The suppository of claim 1 wherein the suppository is rectally-insertable.

9. The suppository of claim 8 wherein the medicinally-acitve ingredients are selected from the group consisting of bisacodyl, aminophylline, acetaminophen and aspirin.

10. The suppository of claim 1 wherein the alginic acid and the effervescent agent together comprise about 24.3 to about 29.7 percent by weight of the composition.

* * * * *